United States Patent [19]
Fare et al.

[11] Patent Number: 5,992,820
[45] Date of Patent: Nov. 30, 1999

[54] FLOW CONTROL IN MICROFLUIDICS DEVICES BY CONTROLLED BUBBLE FORMATION

[75] Inventors: Thomas Louis Fare, Yardley, Pa.; Zhonghui Hugh Fan, Plainsboro; Paul James Heaney, Skillman, both of N.J.

[73] Assignee: Sarnoff Corporation, Princeton, N.J.

[21] Appl. No.: 08/974,258

[22] Filed: Nov. 19, 1997

[51] Int. Cl.$^6$ .................................................. G01N 27/26
[52] U.S. Cl. ...................... 251/129.01; 204/601; 137/124
[58] Field of Search ................ 251/129.01, 11; 137/142, 143, 146, 147, 124, 827; 204/269, 601

[56] References Cited

U.S. PATENT DOCUMENTS

| | | | |
|---|---|---|---|
| 3,782,453 | 1/1974 | Cates et al. | 137/142 X |
| 4,271,119 | 6/1981 | Columbus . | |
| 4,310,399 | 1/1982 | Columbus . | |
| 4,364,228 | 12/1982 | Eller | 137/143 X |
| 4,381,645 | 5/1983 | Galuska | 137/147 X |
| 4,426,451 | 1/1984 | Columbus . | |
| 4,601,881 | 7/1986 | Webster | 422/67 X |
| 4,676,274 | 6/1987 | Brown . | |
| 4,756,884 | 7/1988 | Hillman et al. | 422/73 |
| 5,580,523 | 12/1996 | Bard | 422/50 |
| 5,603,351 | 2/1997 | Cherukuri et al. | 204/269 X |
| 5,660,703 | 8/1997 | Dasgupta | 204/601 |
| 5,785,831 | 7/1998 | Bek | 204/601 X |
| 5,838,351 | 11/1998 | Weber | 251/11 X |
| 5,846,396 | 12/1998 | Zanzucchi et al. | 204/601 |
| 5,858,193 | 1/1999 | Zanzucchi et al. | 204/601 |

FOREIGN PATENT DOCUMENTS

| | | | |
|---|---|---|---|
| 0266375 | 10/1989 | Japan | 215/129.01 |
| 404257008 | 9/1992 | Japan | 251/129.01 |
| 879323 | 10/1961 | United Kingdom | 137/124 |

*Primary Examiner*—Denise L. Ferensic
*Assistant Examiner*—Meredith H. Schoenfeld
*Attorney, Agent, or Firm*—William J. Burke

[57] ABSTRACT

Provided is a fluid control device comprising: (a) a channel of capillary dimensions for conveying a liquid, (b) a bubble-forming device for forming a channel-blocking bubble in the channel, wherein such a bubble formed in the channel impedes the flow of the liquid through the channel.

14 Claims, 6 Drawing Sheets

FLOW CONTROL IN MICROFLUIDICS DEVICES BY CONTROLLED BUBBLE FORMATION

The present invention relates to methods of controlling flow in small-scaled liquid distribution systems where the channels for distributing liquid are small enough so that a bubble formed at an appropriate point, including a narrowed region of a channel, can inhibit flow in that channel. The bubbles are formed by applying a bubble-forming voltage to electrodes positioned at the intended site of bubble formation.

A number of related applications have been filed on liquid distribution systems that use electrode-based pumps including U.S. application Ser. No. 08/454,771, filed May 31, 1995 (SAR 11402B); Ser. No. 08/454,772, filed May 31, 1995 (SAR 11402E); Ser. No. 08/454,768, filed May 31, 1995 (SAR 11402F); U.S. Pat. Nos. 5,585,069; 5,593,838; 5,643,738; 5,681,484, 5,846,396; 5,632,876; and 5,858,193. These applications are hereby incorporated herein by reference in their entirety. Other related applications have been filed relating to conducting parallel reactions in small volume including U.S. Pat. Nos. 5,882,903; and 5,863,502. These applications are hereby incorporated herein by reference in their entirety. U.S. application Ser. No. 08/821,480, filed Mar. 21, 1997 (SAR 12337) describes a useful way of operating electrode-based pumps to minimize bubble formation at the electrodes, and this application is also hereby incorporated herein by reference in its entirety.

Such systems that are pumped with electrode-based pumps ("electrokinetic" pumps) having no moving parts can be used for example to relay liquids in very small devices to conduct multiple parallel but non-equivalent small-scale syntheses or to conduct multiple small-scale analytical reactions.

In operating such systems having no moving parts, applicants and their coworkers have utilized systems having capillary barriers (defined below) where flow-inhibiting meniscuses are formed. The capillary barriers hold liquids in place until, for example, a pump is operated to move the liquid past a given capillary barrier, usually into a reaction cell. By the present invention, bubbles are created in flow control positions in liquid-conveying channels. Although the present inventors' work has focused on liquid conveying systems that operate with electrode-based pumps, the invention is more broadly applicable, for instance to systems that operate purely on the basis of capillary flow or operate under the control of mechanical pumping systems. Further, devices that controllably insert channel-traversing bubbles into a channel can be used to create diffusion barriers between segments of liquid in the channel.

SUMMARY OF THE INVENTION

The invention provides a fluid control device comprising: (a) a channel of capillary dimensions for conveying a liquid; (b) a bubble-forming device for forming a channel-blocking bubble in the channel, wherein such a bubble formed in the channel impedes the flow of the liquid through the channel. Preferably, the channel is formed in a substrate. In another preferred embodiment, the bubble-forming device comprises a gas reservoir from which a bubble-forming amount of gas is interjected into the channel. Preferably, the fluid control device further comprises: (c) a pumping device for pumping a liquid through the channel, wherein the fluid control device is operated by forming the channel-blocking bubble while the pump is not operating, thereby limiting undesired flow while the pumps are inactive. Preferably, the pumping device comprises an electrode-based pump.

In a preferred embodiment, the bubble-forming device comprises: (d) two or more electrodes; and the fluid control device further comprises: (e) a power source for applying sufficient voltage to the electrodes to form the bubble (for example by heating or forming gas by electrolysis). Preferably, the fluid control device is operated by forming the channel-blocking bubble while any associated pump is not operating, the bubble thereby limiting undesired flow while the pumps are inactive.

In another preferred embodiment, the bubble-forming device comprises: (g) a electrode intersecting the channel and coated with polymer that is reversibly convertible from a conductive to a neutral state through an electrochemical oxidation or reduction reaction, wherein such conversion renders the polymer relatively more hydrophobic or more hydrophilic; and (h) a source of blocking fluid, wherein, for example depending on the liquid in the channel, the liquid draws away from either the relatively hydrophilic or the relatively hydrophobic polymer surface, thereby drawing blocking fluid into the channel to block liquid flow.

The invention further provides a liquid distribution system comprising a plurality of liquid reservoirs, a plurality of reaction sites, and a network of channels of capillary dimensions, each having a fluid control device of claim 1, such that each reaction site can receive liquid from at least two separate reservoirs. Preferably, at least one fluid control device of claim 1 acts to reproducibly form a capillary barrier that is used in conjunction with one of the pumps to control the flow of liquid in the liquid distribution system.

Definitions capillary dimensions

"Capillary dimensions" are dimensions that favor capillary flow of a liquid. Typically, channels of capillary dimensions are no wider than about 1.5 mm. Preferably channels are no wider than about 500 mm, yet more preferably no wider than about 250 mm, still more preferably no wider than about 150 mm.

capillary barrier

A "capillary barrier" is a barrier to fluid flow in a channel comprising an opening of the channel into a larger space designed to favor the formation, by liquid in the channel, of an energy minimizing liquid surface, such as a meniscus, at the opening.

DETAILED DESCRIPTION

Liquid Distribution Systems

Figure 1:
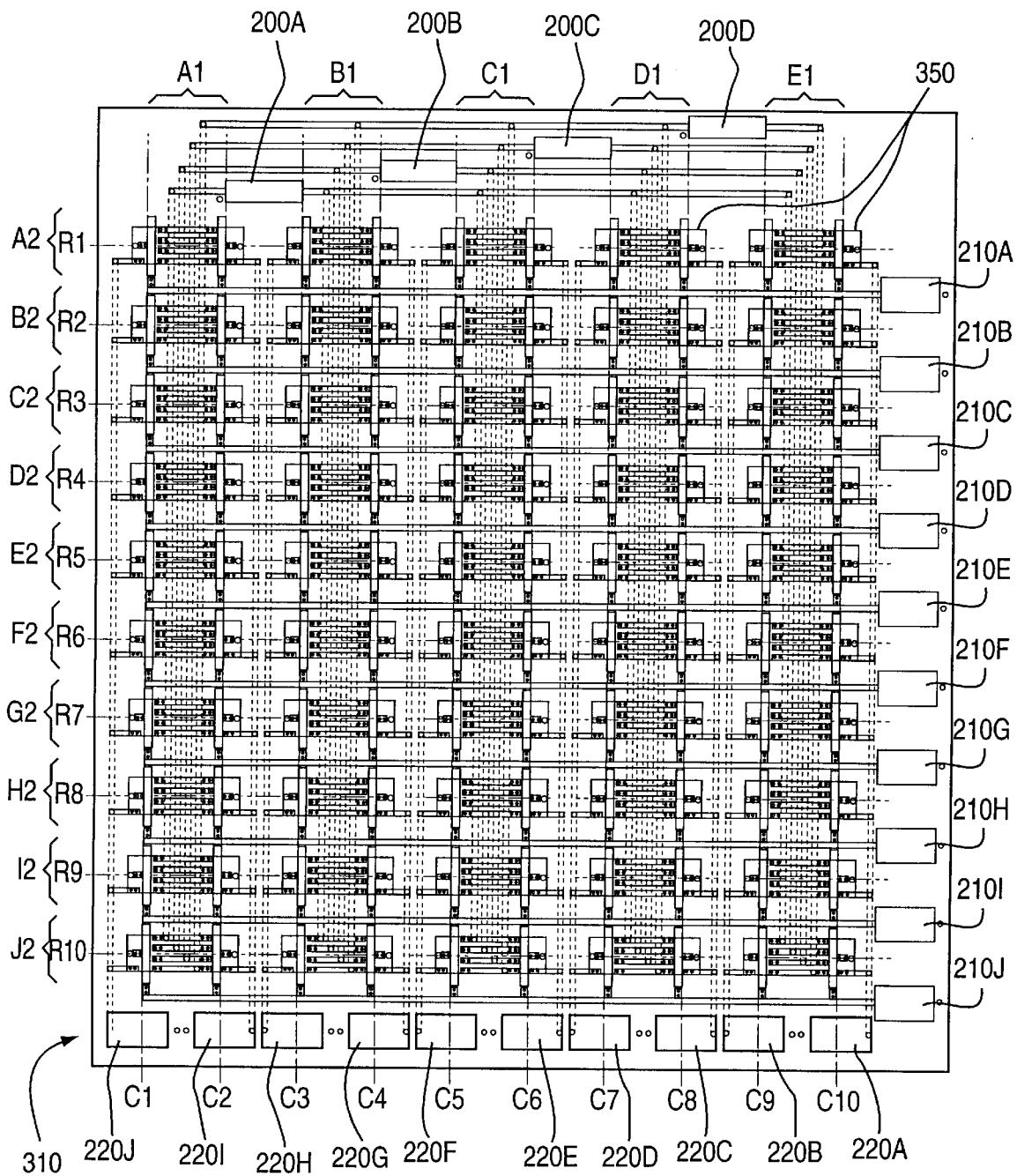
FIG. 1 displays a distribution plate according to the invention.
Figure 2:
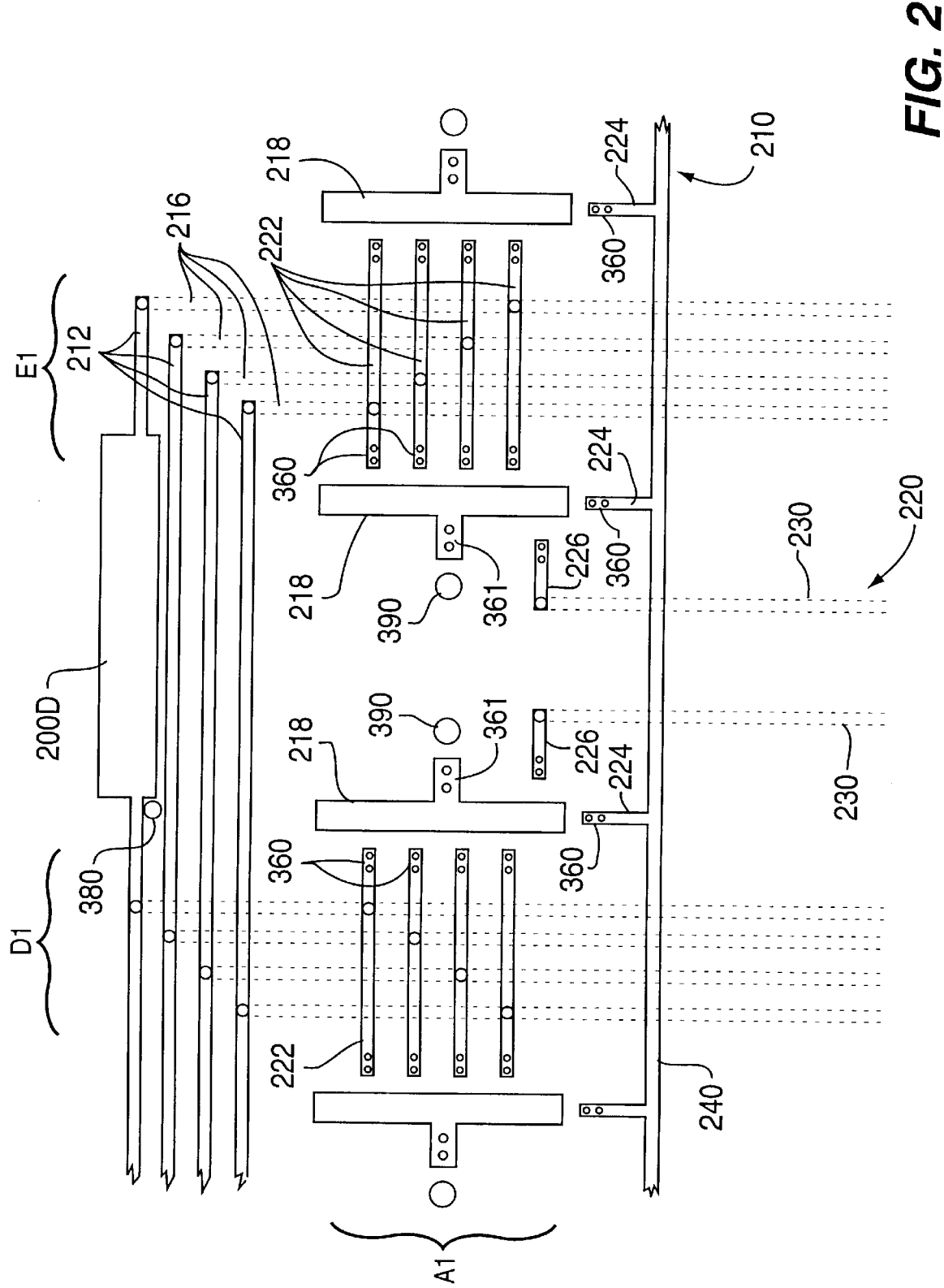
FIG. 2 displays an expanded view of a portion of the distribution plate of FIG. 1.

Recently, a liquid distribution system has been described that uses electrode-based pumps to selectively move a variety of liquid-phase reactants to any of a large number of reaction sites. Illustrative of such liquid distribution systems is the apparatus formed of several plates of substrate that is illustrated in FIGS. 1–3. The description herein of this system is abbreviated since more extensive description can be found in PCT Application No. WO95/14590, filed Nov. 9, 1995 and in U.S. application Ser. No. 08/744,386, filed Nov. 7, 1996. In FIG. 1, reservoirs 200A–200D are connected to reservoir extension channels 212. Connected to extension channels 212 are first, second, third, fourth and fifth sets A1–E1, each set having first, second, third and fourth feeder channels 216. The ceilings of these feeder channels are located in a horizontal plane beneath the floors of the extension channels 212. Via these extension channels, fluid from each of the four first fluid reservoirs 200A–200D can be brought to a location adjacent to any of for example one hundred reaction cells 350 into which the fluid can be moved under the control of pumps or valves. Note that reaction cells 350 are located in a lower horizontal plane than first, second, third and fourth feeder channels 216. Other geometries by which a large number of reaction cells can be addressed by separated fluid reservoirs are described below. In one preferred embodiment, the reservoirs are directly connected, for example with tubing such as plastic or stainless steel tubing to an external reservoir, which can be maintained under a pressurized blanket of gas.

Typically, the liquid distribution system of the invention will be formed of at least three layers such as a feedthrough plate, a distribution substrate and a reaction cell plate. The feedthrough plate is typically bonded to the distribution substrate using one of the methods described below. The reaction cell plate is typically removably fitted to the underside of the distribution substrate, or the underside of an intermediate plate interposed between the distribution substrate and the reaction cell plate.

FIG. 1 shows the layout of features etched into a distribution substrate according to the invention. FIG. 2 shows an expanded view of a portion of a distribution substrate that better illustrates some of the features obscured by the scale of FIG. 1. Typically, the structures indicated in solid lines will be formed in the top layer of the distribution substrate, while the structures indicated with dotted lines will be formed in the bottom layer of the distribution substrate or along the junction between the distribution substrate and the intermediate plate, except that in FIG. 1 the reaction cells 350 are indicated by boxes in solid lines even thought these structures are located in a lower plane. Where appropriate, vertical channels connect the structures in the top of the distribution substrate with those in the bottom. For convenience, the axis from the top of the illustration to the bottom is designated the NS axis, while the axis from right to left is the EW axis.

At the top of FIG. 1 are four first fluid reservoirs 200A, 200B, 200C and 200D. Each of these first fluid reservoirs 200A, 200B, 200C and 200D has two first reservoir extensions 212 extending along substantially all of an EW axis of the distribution substrate. The ceilings of the first reservoir extensions 212 preferably are at substantially the same elevation as the first fill level. At five staggered locations, A1, B1, C1, D1 and E1, along the EW axis of the first reservoir extensions 212 there are four first vertical channels that connect the first reservoir extensions 212 with four first horizontal feeder channel segments 216 that are formed in the bottom layer of the distribution substrate. At each staggered location A1, B1, C1, D1 or E1, four adjacent first horizontal feeder channel segments 216, which are connected to separate first reservoir extensions 212, extend along an NS axis to ten positions, A2, B2, C2, D2, E2, F2, G2, H2, I2 and J2. At each position A2, B2, C2, D2, E2, F2, G2, I2 or J2 along the course of each such set of four adjacent first horizontal feeder channel segments 216, these first horizontal feeder channel segments 216 run between a pair of reaction cells 350. At these positions A2, B2, C2, D2, E2, F2, G2, H2, I2, or J2, the four adjacent first horizontal feeder channel segments 216 are separately connected, via separate second vertical channels, to each of four perpendicular first distribution channels 222 formed in the top layer of the distribution substrate.

In the illustrated embodiment, liquid is fed into the fluid reservoir 200 through channels in the feedthrough plate and such liquid that is not needed to fill the fluid reservoirs to the defined level is drained through drains 380. Openings are formed in the bottom layer of the feedthrough plate to create a liquid connection or sluice between the first fluid reservoirs 200 and the drains 380. Where the reservoirs are pressurized, the drains are generally not desirable unless for example the drains are connected to a pressure regulatory mechanism such as a pressure relief valve. Liquids are maintained in the first fluid reservoirs 200 (as well as the second fluid reservoirs 210 and third fluid reservoirs 220) typically by the use of an external pump 15 (not shown). In other embodiments the fluid in the reservoirs is maintained with a hydrostatic pressure. Alternatively, a defined level can be maintained by monitoring the level of liquid in the first fluid reservoirs 200 (or second fluid reservoirs 210 or third fluid reservoirs 220) and only activating the pumps feeding liquid to a given fluid reservoir when needed to maintain the defined level.

Each set of four adjacent first distribution channels 222 are adjacent to two buffer channels 218, located to each side of the first distribution channels 222 along the EW axis. The buffer channels are optional and illustrate but one of bringing diverse liquid feeds to the vicinity of a reaction cell 350. Buffer channels 218 can be avoided by providing for direct conduits from the outlets of distribution channels (which outlets are preferably capillary barriers) to the appropriate reaction cell 350. Liquid can be pumped from any first distribution channel 222 into the adjacent buffer channel 218 by activating the first pump 360 (indicated in FIG. 2 by two filled dots representing the electrodes of one type of pump) of the first distribution channel 222. This pumping creates additional pressure that moves the liquid over a capillary barrier separating the first distribution channel 222 and the buffer channel 218. Between each first distribution channel 222, second distribution channel 224 or third distribution channel 226 and the adjacent buffer channel 218 and between each buffer channel 218 and its adjacent third vertical channel there is a capillary barrier that inhibits liquid flow when the pumps are not activated. Second openings are formed in the bottom layer of the feedthrough plate to create a liquid connection or sluice between the first distribution channels 222 and the buffer channels 218. From a buffer channel 218, liquid can be pumped using a second pump 361 (indicated in FIG. 2 by two filled dots representing the electrodes of one type of pump) to a third vertical channel that connects with a reaction cell in the reaction cell plate. Third openings in the bottom layer of the feedthrough plate or the distribution substrate serve to create a liquid connection or sluice between the buffer channels 218 and third vertical channels.

Along the right side of the distribution substrate are ten second fluid reservoirs 210, each having a second reservoir extension 240 extending along an EW axis. Second distribution channels 224 form "L"-extensions off of second reservoir extensions 240 and are each positioned adjacent to a separate buffer channel 218, such that there are ten second distribution channels 224 extending off of each second reservoir extension 240. Each second distribution channel 224 has a pump 360 that can move liquid from a second distribution channel 224 to the adjacent buffer channel 218. Second openings in the bottom of feedthrough plate serve to provide a sluice or route of liquid connection between the second distribution channels 224 and the buffer channels 218. Liquid moves from the buffer channels 218 to the reaction cells as described above. Located adjacent to each second reservoir 210 can be a drain that operates to maintain a defined third fill level as described above.

Located along the bottom edge of the distribution substrate illustrated in FIG. 1 are ten third liquid fluid reservoirs 220. Horizontal feeder channel segments 230 are connected to the third fluid reservoirs 220 and to third distribution channels 226 via fourth vertical channels. The third distribution channels 226 have first pumps 360 which can move liquid into adjacent buffer channels 218 via openings in the feedthrough plate. Located adjacent to each third fluid reservoir 220 is a drain (not shown) that operates to maintain a defined fourth fill level as described above. Third fluid reservoirs 220 and connected third distribution channels 226 operate in just the same way as first fluid reservoirs 200 and first distribution channels 222. Those of ordinary skill in the art will readily envision alternative geometries wherein a number of separate third fluid reservoirs 220 can interact with a given buffer channel 218 via a number of third distribution channels 226 positioned adjacent to the buffer channel 218. Located adjacent to each third reservoir 220 can be a drain that operates to maintain a defined third fill level as described above.

The fluid reservoirs (e.g. first, second and third fluid reservoirs 200, 210 and 220) are typically simply expanded (i.e. wider) portions of the connected extension channels. Preferably, the liquid in the fluid reservoirs is maintained from an external source. Replenishment of the liquid in the reservoirs can be continuous, step-wise on a defined schedule, or based on sensor data feed to controller. Drains can be designed to remove any excess fluid added to the reservoir by use of external pump. The fluid reservoirs, filled to the respective fill level, such as to a volume from about 1 $\mu$l to about 5 $\mu$l. Appropriate peristaltic pumps, such as the model number 205U multichannel cassette pump available from Watson-Marlow, Inc., can deliver liquid at rates as low as 1 $\mu$l per second. Such pumps need only be activated for a fraction of a second to adequately recharge a fluid reservoir.

The above discussion describes the distribution system as being formed with a feedthrough plate, distribution substrate and reaction cell plate. However, it will be clear that additional plates can conveniently be incorporated into the distribution system. For instance, a intermediate plate is, in a preferred embodiment, permanently bonded underneath the distribution substrate and interposed between the distribution substrate and the reaction cell plate. The use of this intermediate plate and possibly additional plates allows for much greater flexibility in the design of the channels that form the distribution system.

Any pumping device of suitable dimensions can be used as the internal first pumps 360 or second pumps 361 in the liquid distribution system of the invention. Such pumps can include microelectromechanical systems (MEMS) such as reported by Shoji et al., "Fabrication of a Pump for Integrated Chemical Analyzing Systems," *Electronics and Communications in Japan,* Part 2, 70: 52–59, 1989 or Esashi et al., "Normally closed microvalve and pump fabricated on a Silicon Wafer," *Sensors and Actuators,* 20: 163–169, 1989 or piezo-electric pumps such as described in Moroney et al., "Ultrasonically Induced Microtransport," *Proc. MEMS,* 91: 277–282, 1991. Preferably, however, the first pumps 360 and second pumps 361 have no moving parts. Such first pumps 360 or second pumps 361 can comprise electrode-based pumps. At least two types of such electrode-based pumping has been described, typically under the names "electrohydrodynamic pumping" (EHD) and "electroosmosis" (EO). EHD pumping has been described by Bart et al., "Microfabricated Electrohydrodynamic Pumps," *Sensors and Actuators,* A21–A23: 193–197, 1990 and Richter et al., "A Micromachined Electrohydrodynamic Pump," *Sensors and Actuators,* A29:159–168, 1991. EO pumps have been described by Dasgupta et al., "Electroosmosis: A Reliable Fluid Propulsion System for Flow Injection Analysis," *Anal. Chem.,* 66: 1792–1798, 1994.

Practical considerations for operating pumps that move fluids by means of electrodes in a liquid distribution system, such EO and EHD pumping, are discussed in PCT Application No. WO95/14590, filed Nov. 9, 1995. This same WO95/14590 application describes suitable electrodes, methods for forming such electrodes, and presents theoretical considerations that are believed to provide further guidance on how to operate such pumps.

The reaction cell plate can preferably be reversibly bonded to the adjacent plate by, for instance, assuring that the two surfaces are smoothly machined and pressing the two plates together. Or, for example, the seal between the layers can be formed using a deformable gasket interposed between the layers, such as a is described in WO95/14590.

Fabrication of the plates, substrates, channels, reservoirs, chambers and the like can be conducted as set forth in WO95/14590 and U.S. application Ser. No. 08/744,386, filed Nov. 7, 1996.

In fabricating apparatuses with capillary barriers, care must be taken to assure the alignment of the various small-scaled features. Accordingly, an effort was undertaken to design a capillary barrier that was more forgiving of deviations in alignment. Such a design is reflected in FIG. 3A, which shows a liquid distribution having five plate layers, preferably formed of glass, comprising upper top layer 100A, and lower top layer 100B, upper center layer 110A, lower center layer 110B, and bottom layer 120. Between lower center layer 110B and bottom layer 120 is seal 101. Liquid flows from feeder channel 116, through alpha vertical channel 125, through distribution channel 122, to capillary break 170, which is formed by opening 164, which opens into cavity 162 formed in lower top plate 100B. When pump 160 is activated, liquid is pushed past the capillary break until it begins to fall into beta vertical channel 118 and thereafter into reaction cell 150. Reaction cell 150 has drain 155. It will be recognized from prior description that there can be several openings 164 forming several capillary breaks 170 that lead into beta vertical channel 118.

It has been found that the reproducibility of pumping can be improved by assuring that the capillary break occurs at the site intended. One way to do this is to "reset" the capillary break by injecting gas pressure from gas-source channel 102 to blow gas through beta vertical channel 118 and opening 162 to clear it of any liquid forming unwanted functional capillary breaks. Suitable gas inlets are shown, for example, in FIGS. 3B, 3C 3D and 3E. This gas pressure can back up the liquid in, for instance, the distribution channels 122, without detriment. However, the predominant pathway of gas flow is through the beta vertical channel 118, through reaction cell 150, and out drain 155.

Figure 3A:
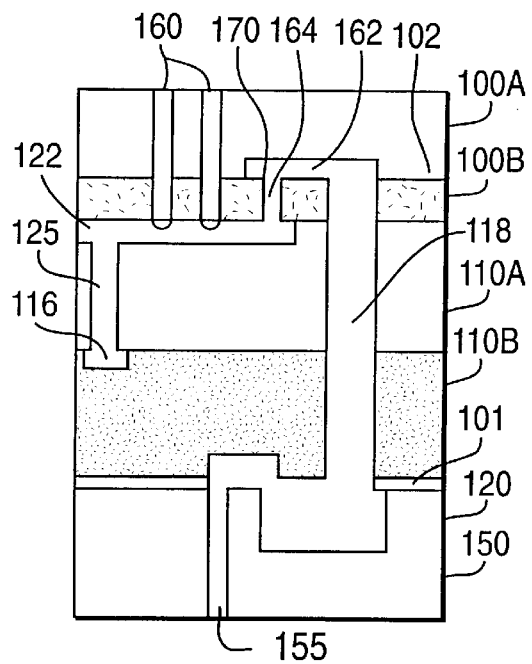
FIGS. 3A, 3B and 3C show a secondary fluid distribution network for non-selectively distributing a fluid to the reaction cells of a liquid distribution system.
Figure 3B:
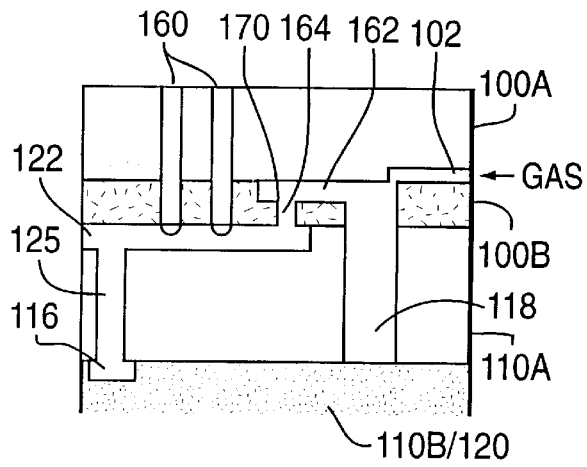
Figure 3C:
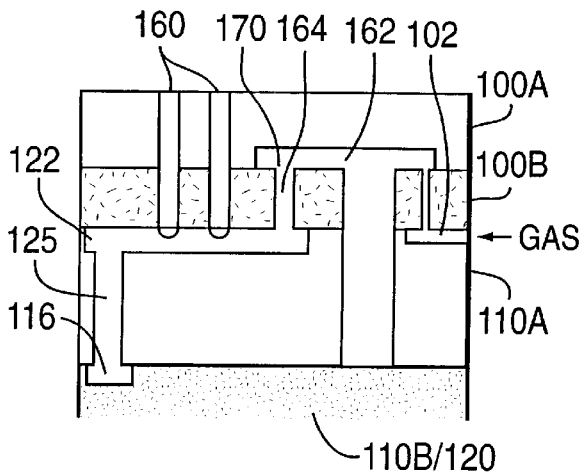
Figure 3E:
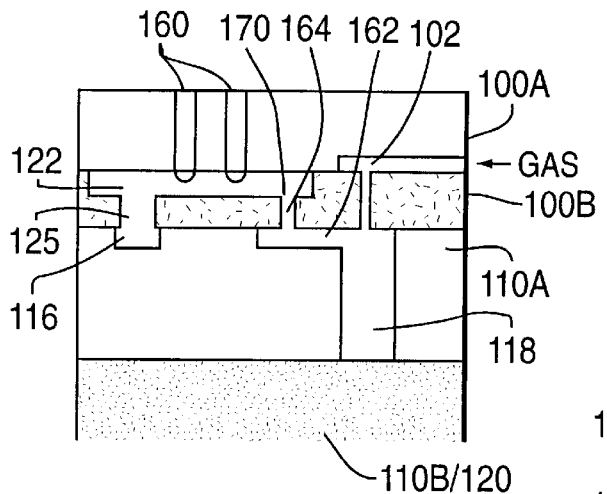
Figure 3D:
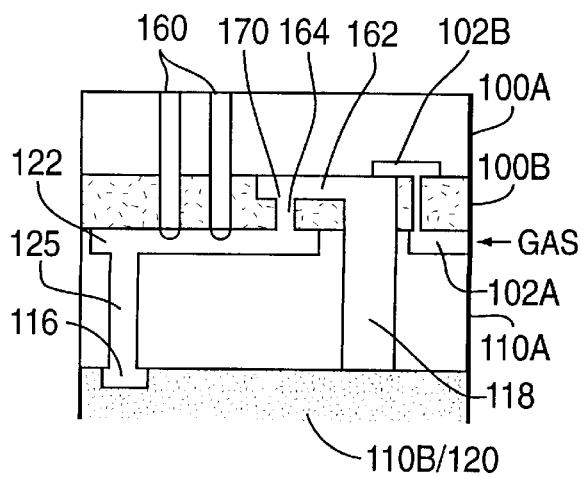

The construction of a liquid distribution system having the capillary breaks of this embodiment as shown in FIG. 3A is generally according to the methods mentioned above, with some refinements pertaining to the upper top layer 100A and lower top layer 100B. For instance in FIG. 3B, the cavities 162 and opening 164 are formed in a plate of relatively larger thickness than the final lower top plate 100B, for instance a thickness of about 8 to about 20 mils. This plate is thinned to become the lower top plate 100B. A gas source channel 102 is formed in the upper top layer 100A. After the two plates 100A and 100B are joined in the manner described above, the combined thickness of the two plates is reduced by lapping. Finally, holes in which the electrodes of pumps 160 are formed are drilled through the joined combination of upper top plate 100A and lower top plate 100B. Typically, the production protocol includes a smoothing process such as lapping to eliminate the fractures that sometimes form at the outbreaks of laser-drilled holes. Other embodiments are shown in FIGS. 3C, 3D and 3E. For the device in FIG. 3E the plates do not have to be pre-joined before drilling holes for electrodes if layer 100B is sufficiently thick to be self-supporting during the fabrication steps.

Electrode-Induced Bubbles

Physical breaks in liquid flowing through channels of capillary dimensions can be created by operating electrodes to create bubbles. These bubbles can be maintained to prevent liquid flow in the channels or to create capillary barriers that can be used in conjunction with electrode-based pumps or other liquid handling devices to selectively control liquid flow in a channel. Further, such bubbles can act as diffusion barriers at the entrance of reaction chambers, or multiple bubbles can be formed to create mobile reaction chambers in channels of capillary dimensions.

In one embodiment of the invention, the bubble is formed to impede an electrical current along the length of the channel. For example, the bubble formation apparatus can be disposed between two electrodes of an electrode-based pump that operate to create a pumping pressure.

Figure 4:
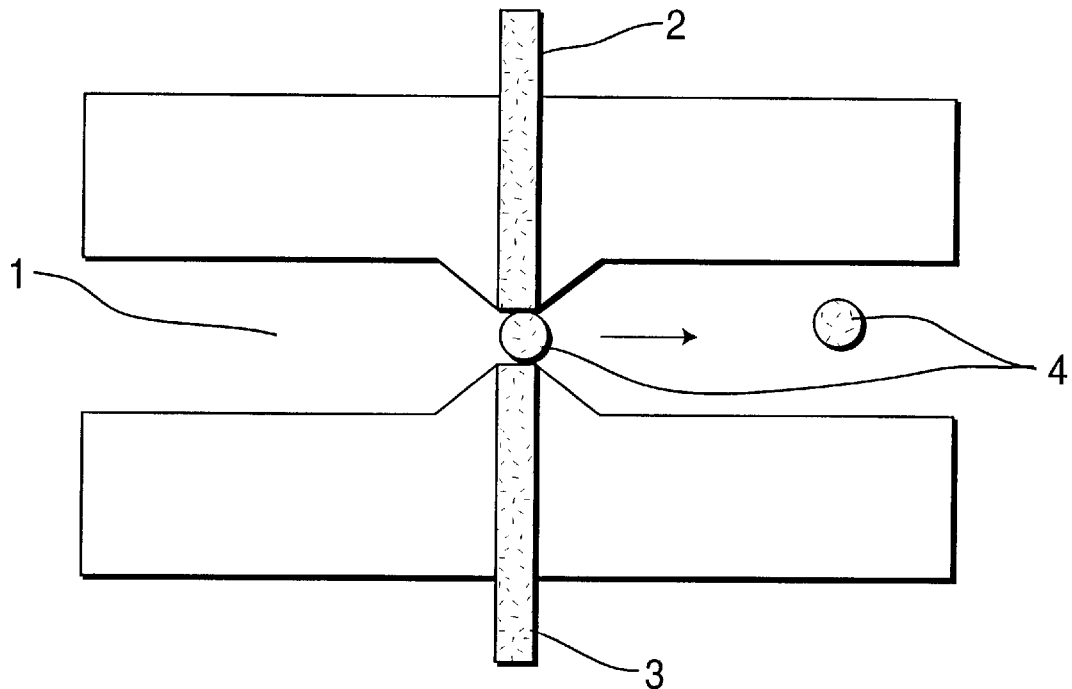
FIG. 4 illustrates a bubble-forming device.

In FIG. 4, a voltage is applied across electrode 2 and electrode 3 to create a bubble 4. The spacing between the electrodes and the channel geometry can be selected to favor the bubble remaining in the gap between electrodes 2 and 3, thereby blocking fluid flow in channel 1. A pulse of extra fluid pressure in the direction indicated by the arrow can be used to dislodge the bubble. In forming the electrodes, in one preferred method solidified via ink (a free-flowing granular material containing conductive material, which granular material can be heat-fused into a conductive solid) forms the base of the electrode. The fluid contacting portion of the electrode is formed by electroplating the end of the base formed of via ink. Such electrode manufacturing processes are described for example in PCT Application No. WO95/14590, filed Nov. 9, 1995 and PCT Application US95/14587, filed November 1995 (titled "Method Of Producing Micro-Electrical Conduits"). FIG. 4 illustrates the electrodes being more closely spaced than the predominant width of the channel 1 by being embedded in protrusions in the sidewalls of the channel. Another way the electrodes can be projected into the channel to narrow the channel is by sufficiently building up the electrode with electroplate. Where the protrusions are embedded in the walls of a channel, they can be formed by etching or molding techniques. For example, dry chemical etching can be used to shape well-defined protrusions in which can be formed channels in which conductors forming the electrodes can be placed. In one such technique, plasma-assisted etching (reactive ion etching), an electrical field can be used to direct the plasma etchant along a given axis, thereby increasing the crispness of the etch boundaries. Dry chemical etching is discussed, for example, in S. M. Sze, "Semiconductor Devices, Physics and Technology", John Wiley & Sons, New York, 1985, pp. 457–465.

Another reason it can be preferable to have the bubble-forming location narrower than the whole of the channel is so that, when pumping pressure is applied to dislodge the bubble, the dislodged bubble takes up only a fraction of the channel width and thus has no adverse impact on fluid flow. Once dislodged, the bubble can proceed to the outlet of the channel or become dissolved in the fluid flowing in the channel. Alternatively, the channels can be designed with traps located above the channels such that upwardly floating bubbles become trapped.

In operating a fluid handling device incorporating a bubble-forming device of the invention to help manage fluid flow, the control electronics preferably turn off the pump when the corresponding bubble-forming device is in operation. The pump thereafter can operate to push fluid past a bubble-forming location.

Figure 5:
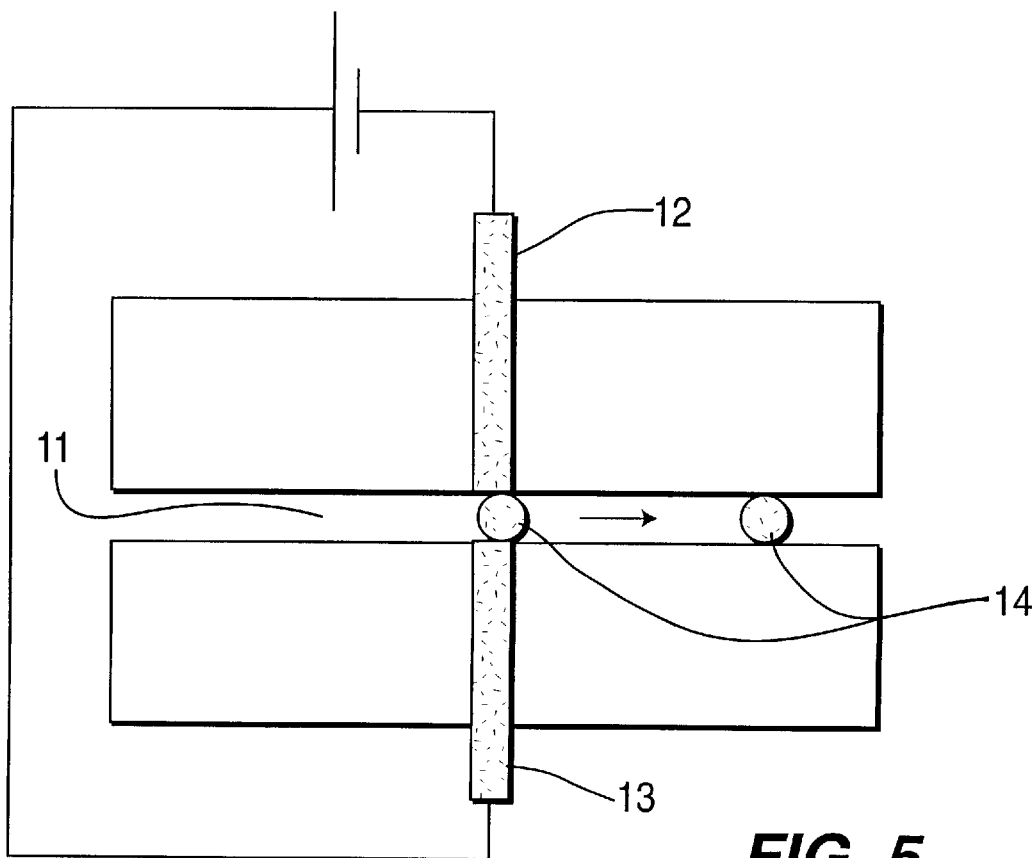
FIG. 5 exemplifies separating plugs of liquid with globules of a second fluid.

FIG. 5 illustrates the situation where the bubbles 14 formed by electrodes 12 and 13 are used to separate plugs of liquid. In these embodiments, preferably either channel geometry is selected to minimize the locations at which bubbles are likely to lodge and disrupt flow, or pumping pressure is high enough to push the bubbles through the channel system.

One method of forming the electrodes so that they align facing one another as in FIG. 4 is to form the channel in a first plate, such as a glass plate, drill a hole in the plate that intersects with the channel and drill a matching hole in a second plate that will be annealed to the first plate to enclose the channel, form conductive vias in the holes with sintered via ink (for instance as described in PCT Application US95/14587, filed November 1995, titled "Method Of Producing Micro-Electrical Conduits"), electroplate the channel-intersecting ends of the vias, and anneal the plates together (for instance using the method described in PCT Application No. US95/14654, filed Nov. 9, 1995, titled "Field-Assisted Sealing"). Substrates, preferably plates, having a thickness of from about 0.1 mm (or about 4 mils) to about 5 mm (or about 200 mils), or from about 0.2 mm (or about 8 mils) to about 5 mm, or from about 0.5 mm (or about 20 mils) to about 2 mm (or about 80 mils) are suitable for forming such vias.

While glass, and particularly a high melting temperature borosilicate glass such as Corning 7740 glass (available from Corning Glass Co., Corning, N.Y.), is a preferred material in which to form the channels and the electrodes, other materials such as plastic (for example, polyethylene, polypropylene, liquid crystal engineering plastics, polyvinylidine fluoride and polytetrafluoroethylene) can also be used.

The channels and electrodes can be formed from multiple layers of materials which are sealed together. For instance, for glass the layers can be sealed by anodic bonding such as that described in PCT Application No. US95/14654, filed Nov. 9, 1995, or U.S. Pat. No. 5,747,169 (U.S. application Ser. No. 08/745,766, filed Nov. 8, 1996).

Figure 6A:
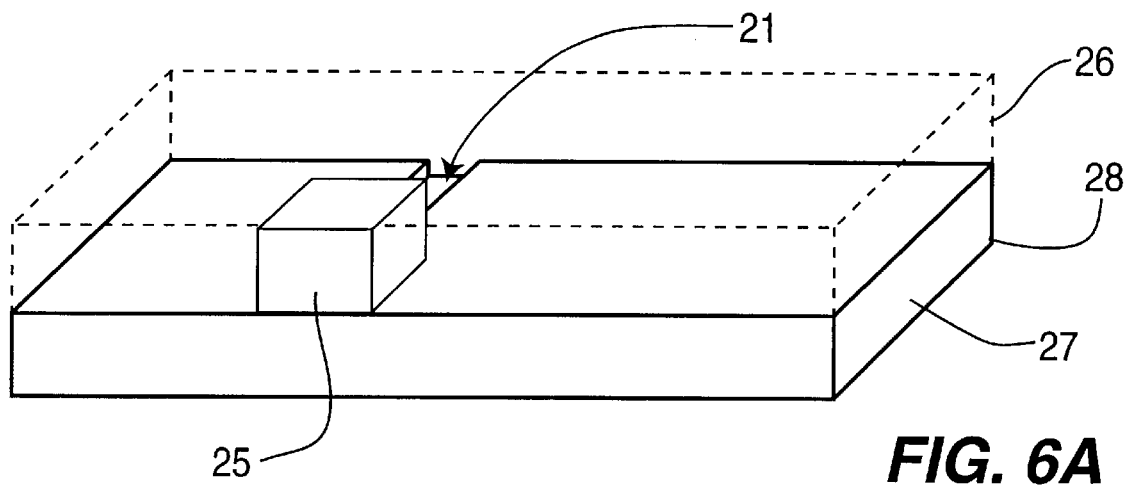
FIG. 6A shows a perspective view of a device for interjecting a channel-blocking fluid from a blocking fluid reservoir.
Figure 6B:
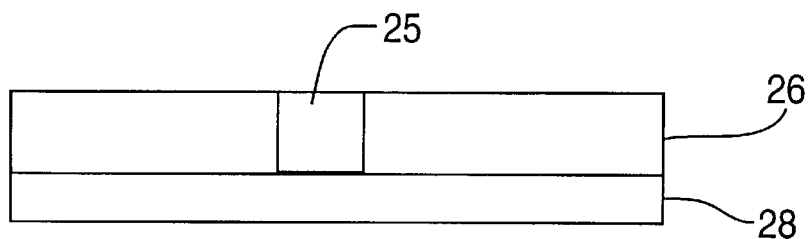
FIGS. 6B and 6C show a side view of the device, without and with an injection of blocking fluid illustrated.
Figure 6C:
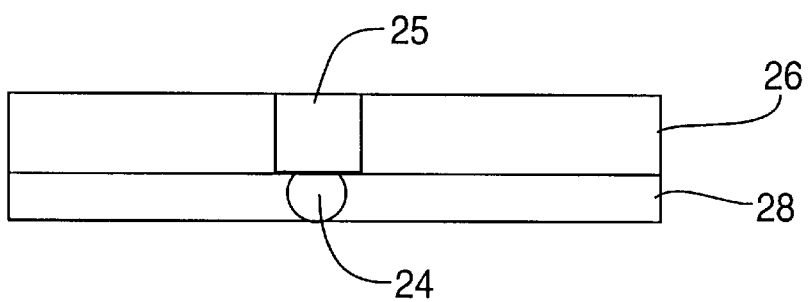

In FIGS. 6A, 6B and 6C, the bubble 24 is drawn from a blocking fluid reservoir 25 adjacent to the channel 21 through the operation for example of a first electrode which can be located on one side of the channel 21 and a matching electrode found on the opposite side of the channel (such as illustrated for electrodes 12 and 13 in FIG. 5). In the Figure, the blocking fluid reservoir 25 is formed in a plate 26. The channel is etched in a plate formed of layers 27 and 28. The surfaces of the electrodes that contact the channel 21 include or are coated with a material that reversibly changes properties such as surface charge, surface energy, or other wetting properties in response to an electrical triggering mechanism. For example, the electrodes are coated with an electro-conducting polymer which is changed to a relatively more hydrophobic form (or to a relatively more hydrophilic form) by an oxidative or reductive reaction, which processes typically convert the polymer between a conductive and a neutral (nonconductive) state. A preferred method of depositing the electro-conducting polymer (such as polythiophene, polypyrrole or polyaniline) is to electropolymerize the monomers onto the electrodes in the channel.

Figure 6D:
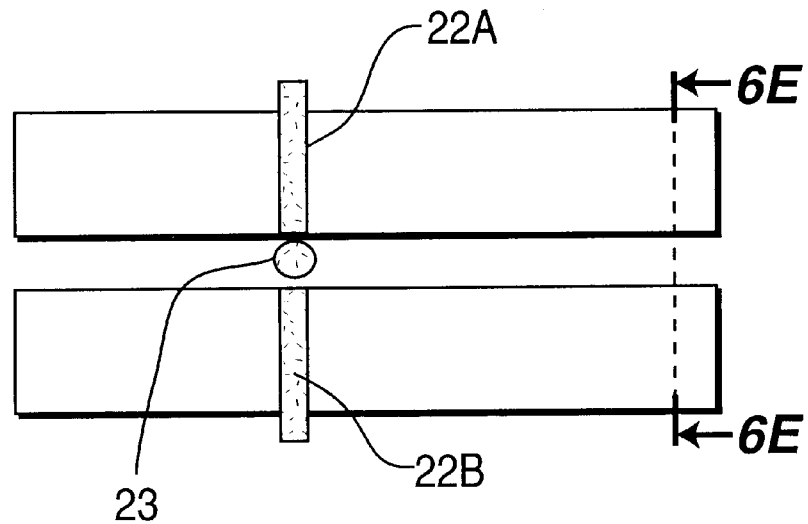
FIGS. 6D and 6E focus on the electrodes of the device.
Figure 6E:
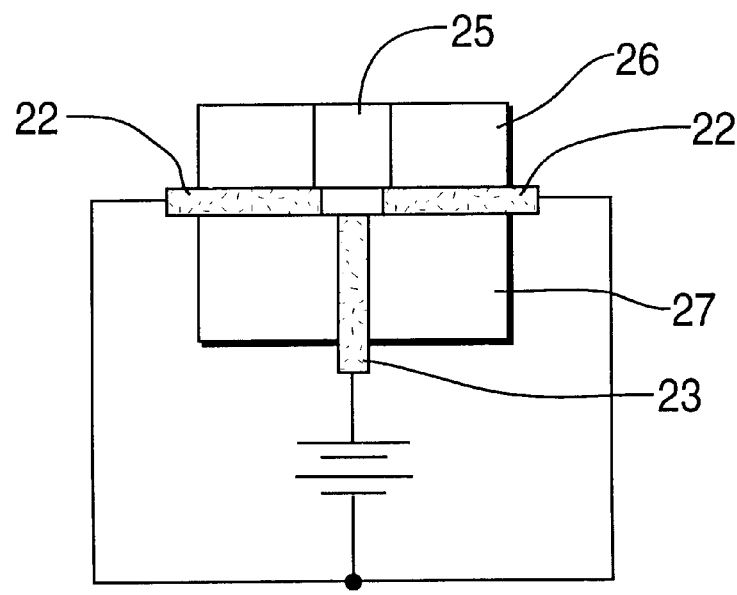

Coated electrodes 22A and 22B are illustrated in FIGS. 6D and 6E. Preferably such coated electrodes are located with sufficient surface area so that the change in surface properties can alter the balance between the channel-blocking fluid of the reservoir 25 and the fluid intended to be moved through channel 21. For example, where the blocking fluid is hydrophobic and the pumped fluid is relatively hydrophilic, conversion of electrode surface to a more hydrophobic form can favor drawing blocking liquid into the channel as illustrated in FIG. 6C. The coated electrode(s) are preferably matched with a working electrode, such as working electrode 23, which is used to initiate the transition of the coated polymer.

Examples of such convertible polymers include polythiophene, polyanilne and polypyrrole, which are conjugated polymers. The corresponding monomers are available from Sigma Chemical Co., St. Louis, Mo.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

We claim:

1. A fluid control device comprising:
   (a) a channel of capillary dimensions for conveying a liquid;
   (b) a bubble-forming device for forming a channel-blocking bubble in the channel comprising two or more electrodes which operate, when sufficient voltage is applied to the electrodes, to form the bubble, wherein such a bubble formed in the channel impedes the flow of the liquid through the channel.

2. The fluid control device of claim 1, wherein the channel is formed in a substrate.

3. The fluid control device of claim 2, further comprising
   (c) a pumping device incorporated into the substrate for pumping a liquid through the channel,
   wherein the fluid control device is operated by forming the channel-blocking bubble while the pump is not operating, thereby limiting undesired flow while the pumps are inactive.

4. The fluid control device of claim 3, wherein the pumping device comprises pump that moves liquid by means of voltage applied to liquid-contacting electrodes.

5. The fluid control device of claim 1, wherein the fluid control device further comprises:
   (d) a power source for applying sufficient voltage to the electrodes to form the bubble.

6. The fluid control device of claim 5, further comprising
   (f) a pumping device for pushing the bubble formed by the bubble-forming device through the channel,
   wherein the fluid control device is operated by forming the channel-blocking bubble while the pump is not operating, thereby limiting undesired flow while the pumps are inactive.

7. The fluid control device of claim 6, wherein the pumping device comprises pump that moves liquid by means of voltage applied to liquid-contacting electrodes.

8. The fluid control device of claim 5, wherein the bubble-forming electrodes are positioned at a narrowed portion of the channel.

9. The fluid control device of claim 1, wherein the bubble-forming device comprises:
   (g) a electrode intersecting the channel and coated with polymer that is reversibly convertible from a conductive to a neutral state through an electrochemical oxidation or reduction reaction, wherein such conversion renders the polymer relatively more hydrophobic or more hydrophilic; and
   (h) a source of gas;
   wherein, depending on the liquid in the channel, the liquid draws away from either the relatively hydrophilic or the relatively hydrophobic polymer surface, thereby drawing blocking fluid into the channel to block liquid flow.

10. The fluid control device of claim 8, further comprising
    (i) a pumping device for pumping a liquid through the channel;
    wherein the fluid control device is operated by forming the channel-blocking bubble while the pump is not operating, thereby limiting undesired flow while the pumps are inactive.

11. The fluid control device of claim 10, wherein the pumping device comprises pump that moves liquid by means of voltage applied to liquid-contacting electrodes.

12. A liquid distribution system comprising a plurality of liquid reservoirs, a plurality of reaction sites, and a network of channels of capillary dimensions, each having a fluid control device of claim 1, such that each reaction site can receive liquid from at least two separate reservoirs.

13. The liquid distribution system of claim 11, where at least one fluid control device of claim 1 acts to reproducibly form a capillary barrier that is used in conjunction with one of the pumps to control the flow of liquid in the liquid distribution system.

14. A method of creating a diffusion barrier between segments of a liquid in a channel of capillary dimensions comprising:
    operating a bubble-forming device for forming multiple channel-traversing bubbles in the channel to separate multiple segments of liquid.

* * * * *